US009149207B2

(12) United States Patent (10) Patent No.: US 9,149,207 B2
Sauter et al. (45) Date of Patent: Oct. 6, 2015

(54) ANNULOPLASTY SIZERS FOR MINIMALLY INVASIVE PROCEDURES

(71) Applicant: Sorin Group USA, Inc., Arvada, CO (US)

(72) Inventors: Joseph A. Sauter, Arvada, CO (US); W. Clark Hargrove, III, Haverford, PA (US)

(73) Assignees: Sorin Group USA, Inc., Arvada, CO (US); The Trustees of the University of Pennsylvania, Philadelphia, PA (US)

( * ) Notice: Subject to any disclaimer, the term of this patent is extended or adjusted under 35 U.S.C. 154(b) by 57 days.

(21) Appl. No.: 14/055,661

(22) Filed: Oct. 16, 2013

(65) Prior Publication Data

US 2014/0046219 A1 Feb. 13, 2014

Related U.S. Application Data

(62) Division of application No. 12/732,656, filed on Mar. 26, 2010, now abandoned.

(60) Provisional application No. 61/163,732, filed on Mar. 26, 2009.

(51) Int. Cl.
*A61B 5/107* (2006.01)
*A61F 2/24* (2006.01)
(Continued)

(52) U.S. Cl.
CPC ............. *A61B 5/1076* (2013.01); *A61B 5/4836* (2013.01); *A61B 6/12* (2013.01); *A61B 17/00234* (2013.01); *A61F 2/2496* (2013.01); *A61F 2250/0098* (2013.01)

(58) Field of Classification Search
CPC ... A61F 2/2496; A61F 2/2448; A61F 2/2466; A61F 2/2445; A61F 2/2442; A61B 19/46; A61B 2019/461

USPC .......................................................... 600/587
See application file for complete search history.

(56) References Cited

U.S. PATENT DOCUMENTS 3,363,442 A 1/1968 Kennedy et al.
5,042,161 A 8/1991 Hodge
(Continued)

FOREIGN PATENT DOCUMENTS

DE 29911694 U1 9/1999
DE 102004019254 B3 11/2005
(Continued)

OTHER PUBLICATIONS

EP Communication issued in EP 07112385 on Jul. 30, 2009.
(Continued)

*Primary Examiner* — Adam J Eiseman
(74) *Attorney, Agent, or Firm* — Faegre Baker Daniels LLP (57) ABSTRACT

A sizing plate for sizing a native valve annulus in a patient's heart for either valve replacement or repair during a minimally invasive surgical procedure is shown and described. The sizing plate is generally shaped such that it corresponds to the shape of the native valve annulus. Additionally, a thickness of the sizing plate is such that it can be inserted through a space between the ribs of the patient during the procedure. The sizing plate includes two keyways extending though the plate separated by a bridge. The keyways are sized and shaped such that they are adapted to be engaged by a minimally invasive surgical tool such as a laparoscopic grasper. The keyways in conjunction with the bridge facilitate manipulation of the sizing plate by the grasper from an external location.

12 Claims, 4 Drawing Sheets

(51) Int. Cl.
*A61B 5/00* (2006.01)
*A61B 6/12* (2006.01)
*A61B 17/00* (2006.01)

(56) References Cited

U.S. PATENT DOCUMENTS

| | | | |
|---|---|---|---|
| 5,360,014 A | 11/1994 | Sauter et al. |
| 5,489,296 A | 2/1996 | Love et al. |
| 5,505,689 A | 4/1996 | Kramer et al. |
| 5,522,884 A | 6/1996 | Wright |
| 5,560,487 A | 10/1996 | Starr |
| 5,669,919 A | 9/1997 | Sanders et al. |
| 5,672,169 A | 9/1997 | Verbeek |
| 5,693,066 A | 12/1997 | Rupp et al. |
| 5,698,307 A | 12/1997 | Levy |
| 5,776,187 A | 7/1998 | Krueger et al. |
| 5,800,531 A | 9/1998 | Cosgrove et al. |
| 5,810,873 A | 9/1998 | Morales |
| 5,814,096 A | 9/1998 | Lam et al. |
| 5,885,228 A | 3/1999 | Rosenman et al. |
| 5,947,993 A | 9/1999 | Morales |
| 5,951,540 A | 9/1999 | Verbeek |
| 5,972,016 A | 10/1999 | Morales |
| 6,019,739 A | 2/2000 | Rhee et al. |
| 6,024,737 A | 2/2000 | Morales |
| 6,051,002 A | 4/2000 | Morales |
| 6,063,102 A | 5/2000 | Morales |
| 6,110,200 A | 8/2000 | Hinnenkamp |
| 6,202,272 B1 | 3/2001 | Jackson |
| 6,277,110 B1 | 8/2001 | Morales |
| 6,309,383 B1 | 10/2001 | Campbell et al. |
| 6,350,281 B1 | 2/2002 | Rhee |
| 6,352,547 B1 | 3/2002 | Brown et al. |
| 6,387,117 B1 | 5/2002 | Arnold, Jr. et al. |
| 6,402,780 B2 | 6/2002 | Williamson, IV et al. |
| 6,454,799 B1 | 9/2002 | Schreck |
| 6,481,262 B2 | 11/2002 | Ching et al. |
| 6,506,201 B2 | 1/2003 | Di Caprio et al. |
| 6,510,722 B1 | 1/2003 | Ching et al. |
| 6,598,307 B2 | 7/2003 | Love et al. |
| 6,629,350 B2 | 10/2003 | Motsenbocker |
| 6,678,962 B1 | 1/2004 | Love et al. |
| 6,726,713 B2 | 4/2004 | Schaldach, Jr. et al. |
| 6,730,118 B2 | 5/2004 | Spenser et al. |
| 6,769,161 B2 | 8/2004 | Brown et al. |
| 6,846,324 B2 | 1/2005 | Stobie |
| 6,915,560 B2 | 7/2005 | Austin |
| 6,966,924 B2 | 11/2005 | Holmberg |
| 6,968,607 B2 | 11/2005 | Motsenbocker |
| 6,981,982 B2 | 1/2006 | Armstrong et al. |
| 6,988,881 B2 | 1/2006 | Motsenbocker et al. |
| 7,007,396 B2 | 3/2006 | Rudko et al. |
| 7,021,114 B2 | 4/2006 | Perreault |
| 7,069,794 B2 | 7/2006 | Motsenbocker et al. |
| 7,258,698 B2 | 8/2007 | Lemmon |
| 7,338,484 B2 | 3/2008 | Schoon et al. |
| 7,357,814 B2 | 4/2008 | Gabbay |
| 7,367,984 B2 | 5/2008 | Kulcinski et al. |
| 7,427,291 B2 | 9/2008 | Liddicoat et al. |
| 7,455,690 B2 | 11/2008 | Cartledge et al. |
| 7,857,845 B2 | 12/2010 | Stacchino et al. |
| 8,109,996 B2 | 2/2012 | Stacchino et al. |
| 2001/0049558 A1 | 12/2001 | Liddicoat et al. |
| 2002/0035390 A1 | 3/2002 | Schaldach et al. |
| 2002/0042651 A1 | 4/2002 | Liddicoat et al. |
| 2002/0129820 A1 | 9/2002 | Ryan et al. |
| 2002/0198594 A1 | 12/2002 | Schreck |
| 2003/0114913 A1 | 6/2003 | Spenser et al. |
| 2003/0125805 A1 | 7/2003 | Johnson et al. |
| 2003/0192164 A1 | 10/2003 | Austin |
| 2004/0039436 A1 | 2/2004 | Spenser et al. |
| 2004/0123437 A1 | 7/2004 | Kokish |
| 2004/0193259 A1 | 9/2004 | Gabbay |
| 2004/0225356 A1 | 11/2004 | Frater |
| 2005/0166389 A1 | 8/2005 | Perreault et al. |
| 2005/0197695 A1 | 9/2005 | Stacchino et al. |
| 2005/0197696 A1 | 9/2005 | Gomez Duran |
| 2005/0229670 A1 | 10/2005 | Perreault |
| 2005/0234537 A1 | 10/2005 | Edin |
| 2005/0240256 A1 | 10/2005 | Austin |
| 2005/0267529 A1 | 12/2005 | Crockett et al. |
| 2005/0283232 A1 | 12/2005 | Gabbay |
| 2006/0004469 A1 | 1/2006 | Sokel |
| 2006/0074486 A1 | 4/2006 | Liddicoat et al. |
| 2006/0178740 A1 | 8/2006 | Stacchino et al. |
| 2006/0265855 A1 | 11/2006 | Stenzel |
| 2007/0027534 A1 | 2/2007 | Bergheim et al. |
| 2007/0056346 A1 | 3/2007 | Spenser et al. |
| 2007/0061009 A1 | 3/2007 | Spenser et al. |
| 2007/0100356 A1 | 5/2007 | Lucatero et al. |
| 2007/0162113 A1 | 7/2007 | Sharkawy et al. |
| 2007/0173861 A1 | 7/2007 | Strommer et al. |
| 2008/0262603 A1 | 10/2008 | Giaquinta et al. |
| 2009/0018570 A1 | 1/2009 | Righini et al. |
| 2009/0192602 A1 | 7/2009 | Kuehn |
| 2009/0192603 A1 | 7/2009 | Ryan |
| 2010/0249661 A1 | 9/2010 | Righini et al. |
| 2010/0262043 A1 | 10/2010 | Sauter et al. |
| 2014/0207011 A1 | 7/2014 | Righini et al. |

FOREIGN PATENT DOCUMENTS

| | | | |
|---|---|---|---|
| EP | 0155245 B1 | 5/1990 |
| EP | 0515324 B1 | 11/1992 |
| EP | 0401199 B1 | 1/1995 |
| EP | 0778009 B1 | 7/2002 |
| EP | 1353420 B1 | 3/2005 |
| EP | 1174098 B1 | 3/2006 |
| EP | 1690515 B1 | 7/2008 |
| EP | 1570809 B1 | 1/2009 |
| GB | 2083362 A | 3/1982 |
| JP | 11332997 A | 12/1999 |
| WO | WO9639942 A1 | 12/1996 |
| WO | WO9724989 A1 | 7/1997 |
| WO | WO9814138 A1 | 4/1998 |
| WO | WO9953864 A1 | 10/1999 |
| WO | WO9955255 A1 | 11/1999 |
| WO | WO0006052 A1 | 2/2000 |
| WO | WO9953866 A1 | 2/2000 |
| WO | WO0021464 A1 | 4/2000 |
| WO | WO0030565 A1 | 6/2000 |
| WO | WO0121076 A1 | 3/2001 |
| WO | WO0121097 A2 | 3/2001 |
| WO | WO01076510 A2 | 10/2001 |
| WO | WO0211646 A1 | 2/2002 |
| WO | WO01021110 A1 | 8/2002 |
| WO | WO01021103 A2 | 10/2002 |
| WO | WO02092257 A1 | 11/2002 |
| WO | WO2005082578 A1 | 9/2005 |
| WO | WO2006088712 A1 | 8/2006 |
| WO | WO2006117016 A1 | 11/2006 |
| WO | WO2006127089 A1 | 11/2006 |
| WO | WO2006136930 A1 | 12/2006 |
| WO | WO2007030825 A2 | 6/2007 |
| WO | WO2006007401 A2 | 1/2008 |
| WO | WO2008089365 A2 | 7/2008 |

OTHER PUBLICATIONS

Extended European Search Report issued in EP 07106697, mailed Aug. 21, 2007, 6 pages.
Extended European Search Report issued in EP 07112385, mailed Apr. 1, 2008, 11 pages.
Extended European Search Report issued in EP 10168449, dated Aug. 19, 2010, 3 pages.
International Search Report and Written Opinion issued in PCT/US2010/028873, dated Jun. 15, 2010, 11 pages.
Partial European Search Report issued in EP 07112385, mailed Jan. 4, 2008, 5 pages.

ANNULOPLASTY SIZERS FOR MINIMALLY INVASIVE PROCEDURES

CROSS-REFERENCE TO RELATED APPLICATION

This application is a divisional of U.S. application Ser. No. 12/732,656, filed Mar. 26, 2010, which claims the benefit under 35 U.S.C §119 of U.S. Provisional Application No. 61/163,732, filed on Mar. 26, 2009, which are herein incorporated by reference in their entirety for all purposes.

TECHNICAL FIELD

The present invention relates to devices, kits, and methods for sizing the annulus of an anatomical structure. More particularly, the present invention is related to sizing plates for use in minimally invasive surgical procedures to repair or replace a diseased native valve.

BACKGROUND

A heart valve can become defective or damaged, such as resulting from congenital malformation, disease, or aging. When the valve becomes defective or damaged, the leaflets may not function properly. One common problem associated with a degenerating heart valve is an enlargement of the valve annulus (e.g., dilation). Other problems that may result in valve dysfunction are chordal elongation and lesions developing on one or more of the leaflets. Adverse clinical symptoms, such as chest pain, cardiac arrhythmias, dyspnea, may manifest in response to valve prolapse or regurgitation. As a result, surgical correction, either by valve repair procedures or by valve replacement, may be required.

Surgical reconstruction or repair procedures may include plication, chordal shortening, or chordal replacement. Another common repair procedure relates to remodeling of the valve annulus (e.g., annuloplasty), which may be accomplished by implantation of a prosthetic ring to help stabilize the annulus and to correct or help prevent valvular insufficiency which may result from defect or dysfunction of the valve annulus. Properly sizing and implanting the annuloplasty ring may substantially restore the valve annulus restored to its normal, undilated, circumference. In other situations, the valve can be replaced. During valve replacement procedures, the valve annulus is sized so as to select an appropriately sized replacement valve.

SUMMARY

The present invention relates to devices, kits, and methods for sizing the annulus of an anatomical structure. More particularly, the present invention is related to sizing plates for use in minimally invasive surgical procedures to repair or replace a diseased native valve.

Example 1 is a sizing plate for sizing a native valve annulus in a patient's during a minimally invasive valve replacement repair or procedure. The sizing plate includes an upper surface and a lower surface defining a thickness of the sizing plate between the upper and lower surfaces; first and second keyways extending through the sizing plate from the upper planar surface to the lower planar surface of the sizing plate; and a bridge member between the first and second keyways configured to be engaged by a laparoscopic grasping tool.

Example 2 is a sizing plate according to Example 1, wherein the sizing plate is generally D-shaped.

Example 3 is a sizing plate according to any one of Examples 1-2, wherein the sizing plate has a shape generally corresponding to a shape of the anterior leaflet of the native mitral valve.

Example 4 is a sizing plate according to any one of Examples 1-3, wherein the bridge member comprises a bar coupled to the sizing plate.

Example 5 is a sizing plate according to any one of Examples 1-4, wherein at least a portion of the sizing plate is radiopaque.

Example 6 is a sizing plate according to any one of Examples 1-5, wherein the first and second keyways have a trapezoidal shape.

Example 7 is a sizing plate according to any one of Examples 1-6, wherein the sizing plate is generally D-shaped having a major dimension and a minor dimension, and wherein the bridge is oriented substantially parallel to the major dimension.

Example 8 is a sizing plate according to any one of Examples 1-7, further comprising an aperture extending through the upper and lower surfaces disposed near a lower edge of the sizing plate.

Example 9 is a sizing plate according to any one of Examples 1-8, wherein the thickness of the sizing plate defined between the upper planar surface and the lower planar surface is such that the sizing plate is adapted to be inserted through a space between a patient's ribs when the sizing plate is oriented on an edge.

Example 10 is a kit for sizing a native valve annulus in a patient's heart during a minimally invasive valve replacement or repair procedure. The kit according to Example 10 includes: a plurality of sizing plates of differing size for sizing the native valve annulus, each sizing plate having a shape generally corresponding to a shape of the anterior leaflet of the native mitral valve and having a major dimension and a minor dimension, wherein at least one of the major dimension and the minor dimension varies among the plurality of sizing plates. Each sizing plate further includes: an upper planar surface and a lower planar surface defining a thickness of the sizing plate between the upper and lower planar surfaces; first and second keyways extending through the sizing plate from the upper planar surface to the lower planar surface of the sizing plate; and a bridge between the first and second keyways configured to be engaged by a laprascopic grasping tool.

Example 11 is a kit according to Example 10, wherein the bridge of each sizing plate is oriented substantially parallel to the major dimension Example 12 is a kit according to any one of Examples 10-11, further including a grasping tool.

Example 13 is a kit according to any one of Examples 10-12, wherein each sizing plate is generally D-shaped.

Example 14 is a kit according to any one of Examples 10-13, wherein the first and second keyways of each sizing plate have a trapezoidal shape.

Example 15 is a kit according to any one of Examples 10-14, wherein each of the sizing plates further includes at least one aperture disposed near a lower edge of the sizing plate.

Example 16 is a kit according to any one of Examples 10-15, wherein the thickness of each of the sizing plates is such that the sizing plate is adapted to be inserted through a space between a patient's ribs when the sizing plate is oriented on an edge.

Example 17 is a method of sizing a native valve annulus during a minimally invasive surgical procedure. The method according to Example 17 includes the steps of:

a) creating a surgical access port in an intercostals space in a patient's body;
b) exposing a native mitral valve annulus;
c) inserting a first sizing plate through the surgical access port, the sizing plate including: an upper surface and a lower surface defining a thickness of the sizing plate; first and second keyways extending through the sizing plate from the upper planar surface to the lower planar surface of the sizing plate; and a bridge member between the first and second keyways configured to be engaged by a laparoscopic grasping tool;
d) engaging a the bridge of the sizing plate using a laparoscopic grasping tool inserted through the surgical access port;
e) positioning the sizing plate in the valve annulus;
f) comparing the major and minor dimensions and the shape of the sizing plate to a major and a minor dimension and shape of an anterior leaflet of the mitral valve; and
g) determining the major and minor dimensions and shape of the anterior leaflet of the mitral vale.

Example 18 is a method according to Example 17, further including the steps of: removing the first sizing plate from the patient's body; inserting a second sizing plate through the surgical access port, the second sizing plate comprising a major dimension and a minor dimension and a shape generally corresponding to the shape of the anterior leaflet of the mitral valve; an upper planar surface and a lower planar surface defining a thickness of the sizing plate; and a first keyway and a second keyway to facilitate engagement of a grasping tool with the sizing plate, the first and second keyways generally centered on the sizing plate and extending through the sizing plate from the upper planar surface to the lower planar surface of the sizing plate; and repeating steps c)-g).

Example 19 is a method according to any one of Examples 17-18, further including the step of temporarily suspending the sizing plate through the access port.

Example 20 is a method according to any one of Examples 17-19, further including the step of orienting the first sizing plate on an edge when inserting the first sizing plate through the surgical access port.

DETAILED DESCRIPTION

Figure 1:
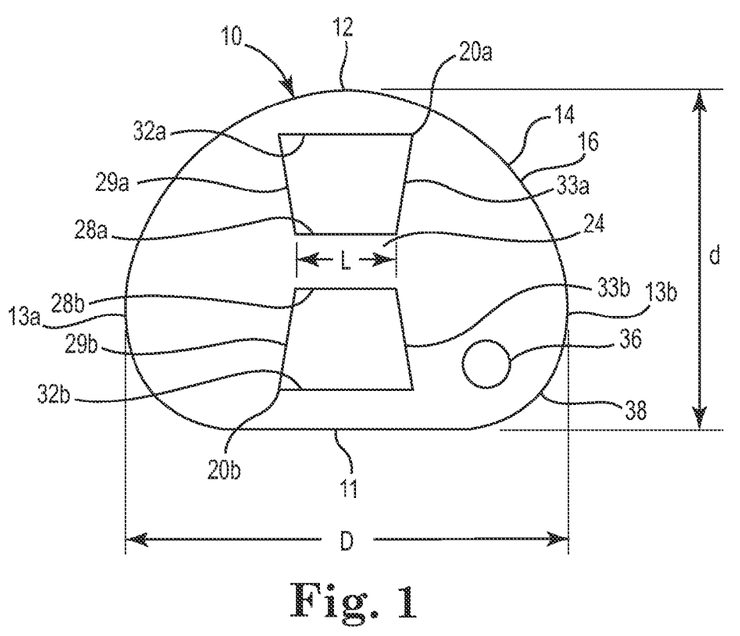
FIG. 1 is a schematic view of a sizing plate according to an embodiment of the present invention.

FIG. 1 is a schematic view of a sizing plate 10 according to various embodiments of the present invention. The sizing plate 10 can be used to determine the size of an annulus of an anatomical structure within a patient's body during a minimally invasive surgical procedure. In the illustrated embodiments, the sizing plate 10 can be used to determine the size of an anterior leaflet of a patient's native mitral valve during a minimally invasive surgical procedure to repair or replace the native valve. Accordingly, the sizing plate 10 generally has a size and shape corresponding to that of the anterior leaflet of the native mitral valve to be repaired. Upon determination of the appropriately sized sizing plate 10, the clinician can then select a corresponding annuloplasty prosthesis, which is then secured to the valve annuls to reshape the annulus to improve coaptation of the anterior and posterior valve leaflets. In some embodiments, the sizing plate 10 includes a substantially straight lower edge 11, an arcuate upper edge 12, and first and second side edges 13a and 13b extending between the substantially straight lower edge 11 and the arcuate upper edge 12. In the illustrated embodiment of FIG. 1, the sizing plate 10 is configured for use in a mitral valve repair procedure, and therefore has the characteristic "D"-shape of a native mitral valve annulus, with orthogonal major and minor dimensions D and d, respectively. In various other embodiments, the sizing plate 10 has a size and shape generally corresponding to the annulus of another cardiac valve, e.g., the aortic valve.

The sizing plate 10 is sized such that it can be inserted through a minimally invasive surgical access port formed in a patient's body. According to various embodiments, the sizing plate 10 is generally planar and includes an upper planar surface 14 and a lower planar surface 16. In some embodiments, a thickness of the sizing plate 10 defined between the upper and lower planar surfaces 14 and 16 facilitates insertion of the sizing plate 10 on its side through a narrow surgical access port. For example, in some embodiments, a thickness of the sizing plate 10 is such that it can be inserted on its side through a space between a patient's ribs. In one embodiment, the sizing plate 10 has a thickness of about 0.125 inches (0.317 cm). In other embodiments, the overall outer size and shape of the sizing plate 10 is small enough such that the sizing plate 10 need not be inserted though a minimally invasive surgical access port on its side, but rather can be inserted face-down through the surgical access port.

As shown in FIG. 1, the sizing plate 10 includes a first keyway 20a and a second keyway 20b extending through the sizing plate 10 from the upper surface 14 to the lower surface 16. The two keyways 20a, 20b are generally centered in the sizing plate 10 and are separated from one another by a bridge 24. In one embodiment, as shown in FIG. 1, the keyways 20a, 20b are formed in the sizing plate 10 as mirror images of one another. The keyways 20a, 20b and the bridge 24 facilitate engagement of a surgical tool with the sizing plate 10, as will be described in further detail below.

In the illustrated embodiment, the size and shape of the keyways 20a, 20b facilitate engagement of the sizing plate by a minimally invasive surgical tool, e.g., a standard laparascopic grasper. Additionally, the dimensions of the keyways 20a, 20b are selected so as to limit movement of the surgical tool within the keyways 20a, 20b, once the surgical tool is engaged with the sizing plate 10.

As further shown, each keyway 20a, 20b has a generally trapezoidal shape. Thus, the shape of the keyway 20a is defined by substantially parallel first and second sides 28a, 32a, and lateral sides 29a, 33a extending between the first and second sides 28a, 32a. Additionally, the keyway 20b has substantially parallel first and second sides 28b, 32b and lateral sides 29b, 33b therebetween. In the illustrated embodiment, the sides 28a, 28b, 32a, and 32b of the keyways 20a, 20b are oriented substantially parallel to the major dimension D of the sizing plate 10, and the keyways 20a, 20b are generally laterally centered on the sizing plate 10.

As shown, the first sides 28a, 28b of the keyways 20a, 20b are generally narrower than the second sides 32a, 32b, respectively, so as to define the illustrated trapezoidal shape of the keyways 20a, 20b. Additionally, the bridge 24 separates the first sides 28a, 32a of the keyways 20a, 20b, and provides a structure which can be gripped by a minimally invasive grasping tool. In one embodiment, the bridge 24 is integrally formed with the sizing plate 10. In another embodiment, the bridge 24 is a separate member that is coupled to the sizing plate 10 during the fabrication of the sizing plate 10. As can be seen in FIG. 1, the bridge 24 has a length L corresponding to the length of the first sides 28a, 32a of the keyways 20a, 20b. As discussed in greater detail below, the dimensions of the keyways 20a, 20b facilitate and guide insertion of the working ends of a surgical tool into secure engagement with the sizing plate 10 while the bridge 24 is gripped by the surgical tool.

According to some embodiments, as shown in FIG. 1, the sizing plate 10 also includes at least one aperture 36 in addition to the keyways 20a, 20b. Like the keyways 20a, 20b, the aperture 36 extends through the sizing plate from the upper surface 14 to the lower surface 16. The aperture 36 can be provided at any location on the sizing plate 10. In one embodiment, the aperture 36 is located at or near a bottom side edge 38 of the sizing plate 10. In another embodiment, two apertures are provided at or near opposite bottom side edges of the sizing plate 10 (shown in FIG. 2 described below). According to various embodiments, a suture can be threaded through the aperture 36 such that the sizing plate 10 can be lowered and/or suspended through a surgical access port formed in the patient's body.

Figure 2:
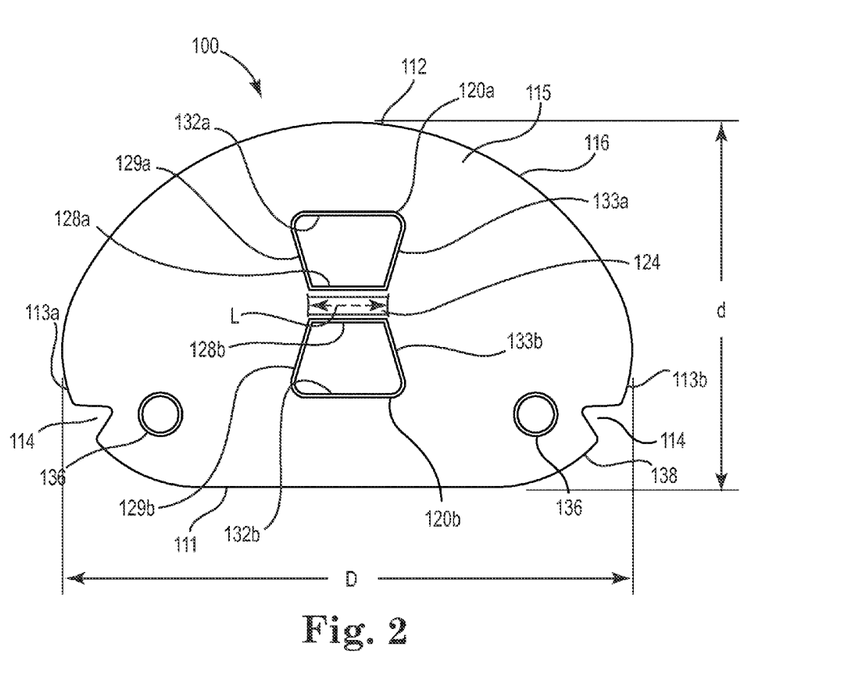
FIG. 2 is a schematic view of a sizing plate according to another embodiment of the present invention.

FIG. 2 is a schematic view of a sizing plate 100 according to another embodiment of the present invention. As described above, the sizing plate 100 is configured for use in a mitral valve repair procedure, and therefore has the characteristic "D"-shape of an anterior leaflet of a native mitral valve, with orthogonal major and minor dimensions D and d, respectively. In various other embodiments, the sizing plate 100 has a size and shape generally corresponding to the annulus of another cardiac valve, e.g., the aortic valve. According to various embodiments, the sizing plate 100 includes a substantially straight lower edge 111, an arcuate upper edge 112, and first and second side edges 113a and 113b extending between the substantially straight lower edge 111 and the arcuate upper edge 112. According to some embodiments, the sizing plate 100 can also include at least one notch 114 formed in one of the edges (111, 112, 113a, 113b) of the sizing plate 100. In one embodiment, as shown in FIG. 2, the sizing plate 100 includes two notches 114, each notch 114 formed in each of the first and second side edges 113a, 113b. The notches 114 can be used by the clinician to orient and align the sizing plate 100 with the native valve annulus.

The sizing plate 100 is sized such that it can be inserted through a minimally invasive surgical access port formed in a patient's body. According to various embodiments, the sizing plate 100 is generally planar and includes an upper planar surface 115 and a lower planar surface 116. In some embodiments, a thickness of the sizing plate 100 defined between the upper and lower planar surfaces 115 and 116 facilitates insertion of the sizing plate 100 on its side through a narrow surgical access port. For example, in some embodiments, a thickness of the sizing plate 100 is such that it can be inserted on its side through a space between a patient's ribs. In one embodiment, the sizing plate 100 has a thickness of about 0.125 inches (0.317 cm). In other embodiments, the overall outer size and shape of the sizing plate 100 is small enough such that the sizing plate 100 need not be inserted though a minimally invasive surgical access port on its side, but rather can be inserted face-down through the surgical access port.

As shown in FIG. 2, the sizing plate 100 includes a first keyway 120a and a second keyway 120b extending through the sizing plate 100 from the upper surface 115 to the lower surface 116. The two keyways 120a, 120b are generally centered in the sizing plate 100 and are separated from one another by a bridge 124. The keyways 120a, 120b and the bridge 124 facilitate engagement of a surgical tool with the sizing plate 100, as will be described in further detail below.

As described above, the size and shape of the keyways 120a, 120b facilitate engagement of the sizing plate by a minimally invasive surgical tool, e.g., a standard laparoscopic grasper. Additionally, the dimensions of the keyways 120a, 120b are selected so as to limit movement of the surgical tool within the keyways 120a, 120b, once the surgical tool is engaged with the sizing plate 100.

As further shown, each keyway 120a, 120b has a generally trapezoidal shape. Thus, the shape of the keyway 120a is defined by substantially parallel first and second sides 128a, 132a, and lateral sides 129a, 133a extending between the first and second sides 128a, 132a. Additionally, the keyway 120b has substantially parallel first and second sides 128b, 132b and lateral sides 129b, 133b therebetween. In the illustrated embodiment, the sides 128a, 128b, 132a, and 132b of the keyways 120a, 120b are oriented substantially parallel to the major dimension D of the sizing plate 100, and the keyways 120a, 120b are generally laterally centered on the sizing plate 100.

As shown, the first sides 128a, 128b of the keyways 120a, 120b are generally narrower than the second sides 132a, 132b, respectively, so as to define the illustrated trapezoidal shape of the keyways 120a, 120b. Additionally, the bridge 124 separates the first sides 128a, 128b of the keyways 120a, 120b, and provides a structure which can be gripped by a minimally invasive grasping tool.

In some embodiments, as shown in FIG. 2, the bridge 124 is a separate member that is coupled to the sizing plate 100. For example, in one embodiment, the bridge 124 is a bar or rod that is insert-molded into the sizing plate 100, as will be described in more detail below. The bar or rod used to fabricate the bridge 124 can be made from a metal, metal alloy or other suitable biocompatible material. In one example, the bar or rod used to form the bridge 124 is a titanium bar or rod. The rod or bar used to form the bridge 124 can have a variety of cross-sections including round, elliptical, square, rectangular or another polygonal cross-section. In one embodiment, the rod or bar has a rectangular cross-section to facilitate an engagement of the bridge 124 by a grasping tool. The bridge 124 formed by the bar or rod has a length L corresponding to the length of the first sides 128a, 128b of the keyways 120a, 120b.

According to some embodiments, as shown in FIG. 2, the sizing plate 100 includes at least two apertures 136 in addition to the keyways 120a, 120b. Like the keyways 120a, 120b, the apertures 136 extends through the sizing plate 100 from the upper surface 115 to the lower surface 116. The apertures 136 can be provided at any location on the sizing plate 100. In one embodiment, the apertures 136 are located at or near a bottom side edge 138 of the sizing plate 100. According to various embodiments, a suture can be threaded through either aperture 136 such that the sizing plate 100 can be lowered and/or suspended through a surgical access port formed in the patient's body.

The sizing plates 10 and 100, described above with reference to FIGS. 1 and 2, can be fabricated from a variety of biocompatible materials. According to some embodiments, the sizing plates 10 and 100 can be fabricated from any lightweight metal or metal alloy. For example, in one embodiment, the sizing plates 10 and 100 can be fabricated from titanium or a titanium alloy. Exemplary metal fabrication techniques that can be used to fabricate the sizing plates 10 and 100 include machining, stamping, and die-punching.

In other embodiments, the sizing plates 10 and 100 can be fabricated from a polymeric or plastic material. In one embodiment, the sizing plates 10 and 100 can be fabricated from a thermoplastic material. Exemplary thermoplastic materials suitable for use in the human body are well known in the art. In one example, the sizing plates 10 and 100 can be fabricated from a polyetherimide such as ULTEM®. In other examples polytetrafluoroethylene (PTFE or TEFLON®) or polyether ether ketone (PEEK) can be used to fabricate the sizing plates 10 and 100. The plastic material can be formed into the sizing plates 10 and 100 using a variety of plastic fabrication techniques including injection molding. In one embodiment, the sizing plates 10 and 100 are injection molded from a thermoplastic material. In a separate step, before the thermoplastic is cured, the bridge 124, as described with reference to FIG. 2, can be insert-molded into the sizing plate 100. Thus, the bridge 124 is not limited to being fabricated from the same material as the sizing plates 10 and 100, but can be selected from a different material and even a different class of material. For example, in some embodiments, the bridge 124 can be a rod or bar made from a metal or metal alloy. In another embodiment, the bridge 124 can be radiopaque.

In some embodiments, the sizing plates 10 and 100 can be fabricated such that at least a portion of the sizing plates 10 and 100 is radiopaque. In one embodiment, an entire sizing plate 10 or 100 is fabricated such that it is radiopaque. The sizing plates 10 and 100 can be made radiopaque by selecting a radiopaque material for fabrication of the sizing plate 10, 100 or by incorporating a radiopaque material into the material used to fabricate the sizing plate 10, 100. By fabricating the sizing plate 10, 100 such that at least a portion of the sizing plate 10, 100 is radiopaque, enable the clinician to easily visualize the sizing plate 10, 100 during the sizing procedure under standard visualization techniques including fluoroscopy and X-ray.

Figure 3:
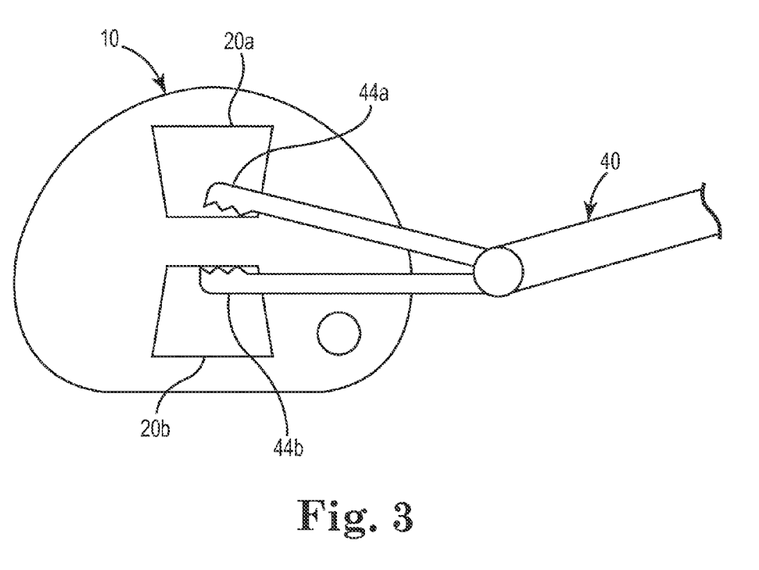
FIG. 3 is a schematic view of a minimally invasive surgical tool engaged with the sizing plate as shown in FIG. 1 according to one embodiment of the present invention.

FIG. 3 is a schematic view of a minimally invasive surgical tool 40 engaged with the sizing plate 10 shown in FIG. 1 according to various embodiments of the present invention. The minimally invasive surgical tool 40 is engaged with the sizing plate 10 to manipulate the sizing plate 10 within a valve annulus or other anatomical structure. The minimally invasive surgical tool 40 facilitates manipulation of the sizing plate 10 from a location external the patient's body under standard visualization techniques. External manipulation of the sizing plate 10 may facilitate easier positioning and rotation of the sizing plate in the body which may result in a more accurate assessment of the shape and size of the valve annulus or other anatomical structure.

Various commercially available, minimally invasive surgical tools may be used with the sizing plate 10. In some embodiments, the minimally invasive surgical tool 40 is a laparoscopic grasper. Such laparoscopic graspers are commercially available from a number of different manufactures and come in a variety of sizes. A grasper facilitates easy manipulation of the sizing plate from an external location. In one embodiment, the minimally invasive surgical tool 40 is a 5 mm grasper.

As shown in FIG. 3, the working ends 44a, 44b of the surgical tool 40, such as, for example, a grasper are inserted into each of the keyways 20a, 20b. As discussed above, the keyways 20a, 20b can be shaped and sized to accommodate insertion of the working ends 44a, 44b of various minimally invasive surgical tools into engagement with the sizing plate 10. The thickness of the sizing plate 10 and the length L and, in some embodiments, the cross-section of the bridge 24 also facilitate engagement of the surgical tool with the plate by providing a sufficient structure for which the working ends 44a, 44b of the tool 40 can grasp. Additionally, in one embodiment, a length L of the bridge 24 provided between the two keyways 20a, 20b, can be slightly greater than a maximum width of each working end 44a, 44b of the surgical tool 40 to be engaged with the sizing plate 10. For example, in one embodiment, if the maximum width of each working end 44a, 44b of the grasper is 5 mm, then the length L of the bridge 24 can be approximately 6 mm.

Figure 4:
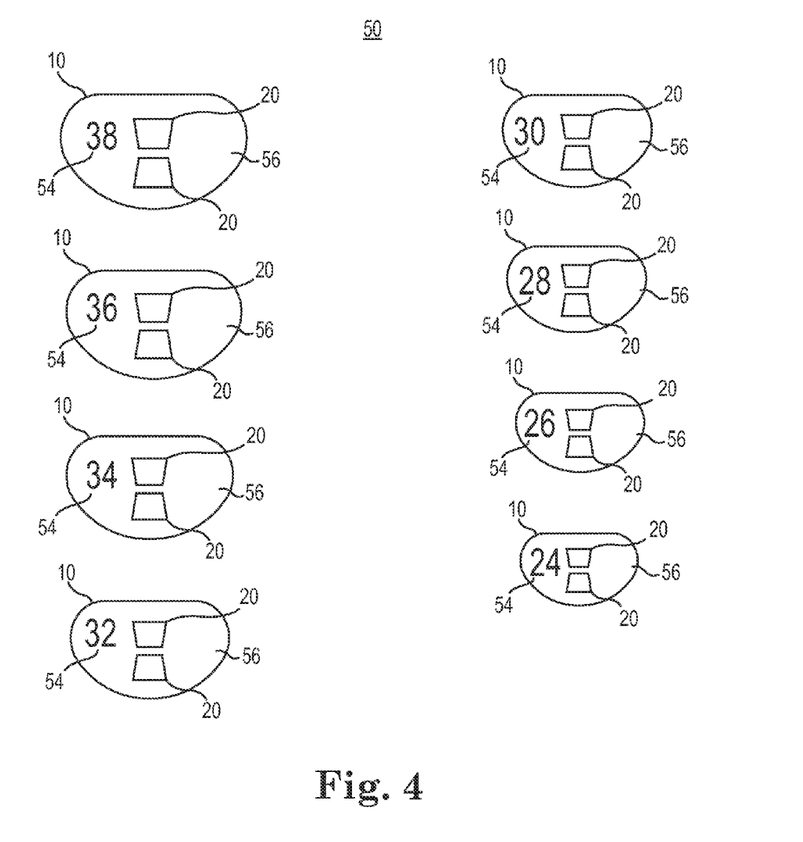
FIG. 4 is a schematic view of a set of sizing plates according to one embodiment of the present invention.

FIG. 4 is a schematic view of a set 50 of sizing plates 10 according to an embodiment of the present invention. The set 50 includes one or more sizing plates 10 of increasing size having the same general shape. According to various embodiments, a maximum height of each plate (corresponding to the minor dimension d of the respective plate) ranges from about 0.657 to about 1.004 inches (from about 1.67 to about 2.55 cm), and a maximum width of each plate (corresponding to the major dimension D of the respective plate) ranges from about 1.020 to about 1.571 inches (from about 2.59 to about 4 cm). In some embodiments, each plate 10 can include a size indicator 54 such as, for example, a number laser-etched, stamped embossed or pad-printed on a plate face 56 indicating the size of the sizing plate 10. In one embodiment, the size indicator 54 can be stamped or pad-printed in radiopaque ink. Table 1 indicates the maximum height and width corresponding to different plate sizes. The maximum height and width are provided in inches (where 1 inch=2.54 cm).

TABLE 1

| Plate Size | Max. Height (Minor Dimension d) | Max. Width (Major Dimension D) |
| --- | --- | --- |
| 24 | 0.657 | 1.020 |
| 26 | 0.714 | 1.098 |
| 28 | 0.762 | 1.176 |
| 30 | 0.813 | 1.256 |
| 32 | 0.862 | 1.334 |
| 34 | 0.910 | 1.412 |
| 36 | 0.960 | 1.493 |
| 38 | 1.004 | 1.571 |

Among a given set 50 of sizing plates 10, the size and shape of the keyways 20 provided in each of the plates 10 remain the same such that they are able to engage with the same size of a minimally invasive surgical tool 40. The set 50 of sizing plates 10 may be provided with or without a minimally invasive surgical grasper tool 40.

A method of using the sizing plate 10 according to the various embodiments discussed above will now be described in reference to FIG. 1. During a minimally invasive surgical procedure to repair or replace a diseased native valve such as the aortic or mitral valve, the surgeon performing the procedure creates a surgical access port in an intercostal space in the patient's body. The surgeon may also create an access port via a mini-sternotomy whereby a piece of the sternum and its corresponding rib are transected to create more space. A selected sizing plate 10 can then be inserted on its side through the access port. In some embodiments, a suture can be inserted through the aperture 36 provided in the plate and can be used to lower the sizing plate 10 on its side through the port. In some embodiments, the suture can be used to temporarily suspend the sizing plate 10 through the access port at the surgical site until the sizing plate 10 is ready for use. Next, the surgeon retracts or excises the valve leaflets using standard techniques to expose the valve annulus. A grasper or other minimally invasive surgical tool 40 capable of engaging the sizing plate 10 is then inserted through the surgical access port and is engaged with the sizing plate 10. The surgical tool 40 is used to position and rotate the sizing plate 10 in the valve annulus such that the size and shape of the valve annulus can be accurately assessed under standard visualization techniques. The surgical tool 40 facilitates external manipulation of the sizing plate in the valve annulus. If the sizing plate 10 is too small or too large when compared to the valve annulus, the sizing plate 10 can be retrieved and removed from the patient's body. In one embodiment, the suture threaded through the aperture 16 provided in the sizing plate 10 is used to remove the sizing plate from the patient's body. A sizing plate 10 of a smaller or larger size is then selected, and the process is repeated until the size of the valve annulus is determined. Once the size of the valve annulus has been determined, the surgeon can proceed with repairing or replacing the valve.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

We claim:

1. A method of sizing a native valve annulus of a mitral valve during a minimally invasive mitral valve repair or replacement procedure comprising:
   creating a surgical access port in an intercostal space in a patient's body;
   exposing the native valve annulus;
   providing a first sizing plate, the first sizing plate including: an upper planar surface and a lower planar surface defining a thickness of the first sizing plate; first and second keyways extending through the first sizing plate from the upper planar surface to the lower planar surface of the first sizing plate; an aperture extending through the upper and lower planar surfaces disposed near a lower edge of the first sizing plate for accommodating a suture threaded through the aperture; and a bridge member between the first and second keyways configured to be engaged by a laparoscopic grasping tool;
   inserting the suture through the aperture in the first sizing plate and using the suture to lower the first sizing plate into the surgical access port;
   engaging the bridge member of the first sizing plate using the laparoscopic grasping tool inserted through the surgical access port;
   positioning the first sizing plate in the native valve annulus;
   comparing a major dimension and a minor dimension and a shape of the first sizing plate to a major dimension and a minor dimension and a shape of an anterior leaflet of the mitral valve; and
   determining the major and minor dimensions and the shape of the anterior leaflet of the mitral valve.

2. The method according to claim 1, further comprising the steps of:
   removing the first sizing plate from the patient's body;
   inserting a second sizing plate through the surgical access port, the second sizing plate comprising a major dimension and a minor dimension and a shape generally corresponding to the shape of the anterior leaflet of the mitral valve; an upper planar surface and a lower planar surface defining a thickness of the second sizing plate; and a first keyway and a second keyway to facilitate engagement of a laparoscopic grasping tool with the second sizing plate, the first and second keyways generally centered on the second sizing plate and extending through the second sizing plate from the upper planar surface to the lower planar surface of the second sizing plate;
   engaging a bridge of the second sizing plate using the laparoscopic grasping tool inserted through the surgical access port;
   positioning the second sizing plate in the valve annulus;
   comparing the major and minor dimensions and the shape of the second sizing plate to the major dimension and the minor dimension and the shape of the anterior leaflet of the mitral valve; and
   determining the major and the minor dimensions and the shape of the anterior leaflet of the mitral valve.

3. The method according to claim 1, further comprising the step of temporarily suspending the first sizing plate through the surgical access port using the suture.

4. The method according to claim 1, further comprising the step of orienting the first sizing plate on an edge when inserting the first sizing plate through the surgical access port.

5. The method according to claim 2, further comprising the step of orienting the second sizing plate on an edge when inserting the second sizing plate through the surgical access port.

6. The method according to claim 1, wherein the first sizing plate is D-shaped.

7. The method according to claim 2, wherein the second sizing plate is D-shaped.

8. The method according to claim 1, wherein the first sizing plate has a shape corresponding to the shape of the anterior leaflet of the native mitral valve.

9. The method according to claim 2, wherein the second sizing plate has a shape corresponding to the shape of the anterior leaflet of the native mitral valve.

10. The method according to claim 1, wherein the bridge member comprises a bar coupled to the first sizing plate.

11. The method according to claim 1, wherein at least a portion of the first sizing plate is radiopaque.

12. The method according to claim 2, wherein at least a portion of the second sizing plate is radiopaque.

* * * * *